United States Patent
Seino et al.

(10) Patent No.: US 6,960,698 B2
(45) Date of Patent: Nov. 1, 2005

(54) METHOD FOR TREATING TAR

(75) Inventors: Mamoru Seino, Ichihara (JP); Shigefumi Tokumasu, Kisarazu (JP)

(73) Assignee: Sumitomo Chemical Compnay, Limted, Osaka (JP)

( * ) Notice: Subject to any disclaimer, the term of this patent is extended or adjusted under 35 U.S.C. 154(b) by 72 days.

(21) Appl. No.: 10/391,620

(22) Filed: Mar. 20, 2003

(65) Prior Publication Data

US 2003/0183557 A1 Oct. 2, 2003

(30) Foreign Application Priority Data

Mar. 27, 2002 (JP) ........................... 2002-088568

(51) Int. Cl.$^7$ .............................. C07C 37/08
(52) U.S. Cl. ..................... 568/768; 568/753
(58) Field of Search ................. 568/768, 753, 568/754

(56) References Cited

U.S. PATENT DOCUMENTS

| | | | |
|---|---|---|---|
| 2,737,480 A | * | 3/1956 | Adams |
| 4,973,766 A | * | 11/1990 | Penzo |
| 5,338,453 A | * | 8/1994 | Fraina |
| 5,962,751 A | | 10/1999 | Dyckman et al. |
| 6,025,530 A | | 2/2000 | Dyckman et al. |
| 6,303,835 B1 | | 10/2001 | Shafer et al. |
| 2001/0025125 A1 | | 9/2001 | Noritake |

* cited by examiner

*Primary Examiner*—Michael L. Shippen
(74) *Attorney, Agent, or Firm*—Sughrue Mion, PLLC

(57) ABSTRACT

A method for treating tar separated from a liquid containing an aromatic hydroxybenzene obtained by acidolysis of a liquid containing an aromatic hydroperoxide, which comprises dissolving the tar with an alkaline aqueous solution.

9 Claims, No Drawings

METHOD FOR TREATING TAR

BACKGROUND OF THE INVENTION

1. Field of the Invention

The present invention relates to a method for treating tar. More particularly, the present invention relates to a method for treating tar separated from a liquid containing an aromatic hydroxybenzene obtained by acidolysis of a liquid containing an aromatic hydroperoxide, wherein the method has advantages in handling, working environments and treatment cost.

2. Description of Related Art

For example, a method for producing an aromatic hydroxybenzene containing the following steps is publicly known:

first step: a liquid containing an alkyl aromatic hydrocarbon is oxidized with air or oxygen in liquid phase, to convert it into a liquid containing an aromatic hydroperoxide, second step: the reaction liquid obtained in the first step is contacted with an alkali aqueous solution, to obtain an aqueous layer containing the aromatic hydroperoxide and an oil layer, third step: the aqueous layer obtained in the second step is contacted with an organic solvent as an extracting solvent, to obtain an aqueous layer and an oil layer containing the aromatic hydroperoxide, fourth step: the oil layer obtained in the third step is contacted with an acid to convert it into a liquid containing an aromatic hydroxybenzene via acidolysis of the aromatic hydroperoxide, and fifth step: the liquid containing the aromatic hydroxybenzene obtained in the fourth step is distilled, to separate tar from low boiling point components containing the organic solvent, and the aromatic hydroxybenzene.

The tar separated as described above has a nature that it solidifies when cooled to 100° C. or lower, and there is a method for treating the tar solidified by cooling, however, depending on the nature of the tar, handling thereof often became very difficult due to stickiness, non-solidification and the like. Further, there were also problems of poor working environments such as odor during handling working of solidified tar, and the like.

SUMMARY OF THE INVENTION

An object of the present invention is to provide, in a method for treating tar separated from a liquid containing an aromatic hydroxybenzene obtained by acidolysis of a liquid containing an aromatic hydroperoxide, a method in which handling of the tar can be markedly improved by dissolving the above-mentioned tar which is itself solid difficult in handling, with an alkaline aqueous solution to give a liquid.

Another object of the present invention is to provide a method for treating tar, having an excellent characteristic that there is no problem about working environments and the treatment can be effected at low cost since hands are not required.

Namely, the present invention relates to a method for treating tar separated from a liquid containing an aromatic hydroxybenzene obtained by acidolysis of a liquid containing an aromatic hydroperoxide, which comprises dissolving the tar with an alkaline aqueous solution.

DETAILED DESCRIPTION OF THE INVENTION

In the present invention, exemplified is a case in which the aromatic hydroperoxide is a di-(2-hydroperoxy-2-propyl) benzene and the aromatic hydroxybenzene is a dihydroxybenzene, and further specifically exemplified is a case in which the aromatic hydroperoxide is 1,3-di-(2-hydroperoxy-2-propyl)benzene and the aromatic hydroxybenzene is 1,3-dihydroxybenzene.

As the tar to be treated in the present invention, tar obtained by the following five steps is exemplified:

first step: a liquid containing an alkyl aromatic hydrocarbon is oxidized with air or oxygen in liquid phase, to convert it into a liquid containing an aromatic hydroperoxide, second step: the reaction liquid obtained in the first step is contacted with an alkali aqueous solution, to obtain an aqueous layer containing the aromatic hydroperoxide and an oil layer, third step: the aqueous layer obtained in the second step is contacted with an organic solvent as an extracting solvent, to obtain an aqueous layer and an oil layer containing the aromatic hydroperoxide, fourth step: the oil layer obtained in the third step is contacted with an acid to convert it into a liquid containing an aromatic hydroxybenzene via acidolysis of the aromatic hydroperoxide, and fifth step: the liquid containing the aromatic hydroxybenzene obtained in the fourth step is distilled, to separate into low boiling point components containing the organic solvent, and tar and the aromatic hydroxybenzene.

The first step is a step in which a liquid containing an alkyl aromatic hydrocarbon is oxidized with air or oxygen in a liquid phase, to convert it into a liquid containing an aromatic hydroperoxide. Specifically, a raw material liquid containing 1,3-diisopropylbenzene (hereinafter, abbreviated as MDC) and 3-isopropyl-1-(2-hydroperoxy-2-propyl) benzene (hereinafter, abbreviated as MHPO) is oxidized with air or oxygen at a temperature of 70 to 110° C. under a pressure of 0 to 1 MPaG (gauge pressure) for a residence time of 0.1 to 50 hours, to obtain 1,3-di-(2-hydroperoxy-2-propyl) benzene (hereinafter, abbreviated as DHPO) and 3-(2-hydroxy-2-propyl)-1-(2-hydroperoxy-2-propyl) benzene (hereinafter, abbreviated as CHPO). As an apparatus, a reaction vessel and reaction column of a flow mode or batch-wise mode can be used.

The second step is a step in which the reaction liquid obtained in the first step is contacted with an alkaline aqueous solution, to obtain an aqueous layer containing an aromatic hydroperoxide and an oil layer. Specifically, it is a step in which the reaction liquid obtained in the first step is extracted with an alkaline aqueous solution, to obtain an alkaline aqueous solution containing DHPO and CHPO. Specific example of the alkaline aqueous solution include a caustic soda aqueous solution and the like, and the concentration is usually 0.1 to 30% by weight. Counter flow single- or multi-stage extraction under conditions of a temperature of 0 to 70° C., a pressure of 0 to 0.5 MPaG and 1 to 10 stages is mentioned, and an extraction column or mixer settler can be used.

The third step is a step in which the aqueous layer obtained in the second step is contacted with an organic solvent as an extracting solvent, to obtain an aqueous layer and an oil layer containing the aromatic hydroperoxide. Specifically, the alkaline aqueous solution containing DHPO and CHPO obtained in the second step is extracted with the organic solvent, to obtain a DHPO solution of the organic solvent, and specific example of the organic solvent includes methyl isobutyl ketone (hereinafter, abbreviated as MIBK). Counter flow single- or multi-stage extraction under conditions of a temperature of 20 to 80° C., a pressure of 0 to 0.5

MPaG and 1 to 10 stages is carried out, and, for example, an extraction column is used.

The fourth step is a step in which the oil layer obtained in the third step is contacted with an acid to convert into a liquid containing an aromatic hydroxybenzene via acidolysis of the aromatic hydroperoxide. Specifically, the DHPO-MIBK liquid obtained in the third step is decomposed with an acid catalyst, to obtain 1,3-dihydroxybenzene, acetone (hereinafter, abbreviated as ACT), tar and the like, and an example of the acid catalyst includes sulfuric anhydride. The decomposition conditions include a temperature of 60 to 100° C., a pressure of 27 to 93 kPa and a residence time of 1 to 15 minutes, and as an apparatus, a column reactor, tubular reactor and a vessel reactor are listed. The reaction can be carried out continuously or batch-wise.

The fifth step is a step in which the liquid containing the aromatic hydroxybenzene obtained in the fourth step is distilled thereby to separate the liquid into tar and the aromatic hydroxybenzene, and a low boiling point component containing the organic solvent. In this step, specifically, from the MIBK solution containing 1,3-dihydroxybenzene, ACT, tar and the like, a low boiling point fraction containing ACT and MIBK and a high boiling point fraction containing 1,3-dihydroxybenzene and tar are first obtained. Next, separation into a fraction containing 1,3-dihydroxybenzene and a fraction containing tar is conducted. The distillation conditions include a temperature of 180 to 220° C. and a pressure of 1 to 30 kPa, and as an example of an apparatus, a fractionating column is listed.

The present invention is characterized in that tar separated is dissolved in an alkaline aqueous solution. By this, the above-mentioned problems can be completely solved by the present invention.

As the alkaline aqueous solution, aqueous solutions of sodium hydroxide (caustic soda), potassium hydroxide and calcium hydroxide are mentioned, and from the economical viewpoint, a caustic soda aqueous solution is preferable. Further, it is preferable that the alkaline aqueous solution has an alkali concentration of 1 to 40% by weight. When the concentration is less than 1% by weight, a caustic soda aqueous solution becomes necessary in large amount, and increase in drain treatment amount sometimes leads to high cost, on the other hand, when the concentration is more than 40% by weight, handling of the alkaline aqueous solution or an aqueous solution after treatment becomes difficult in some cases.

Regarding the conditions and methods for dissolving tar, the following matters are mentioned. A caustic soda aqueous solution and tar are mixed in a vessel for dissolving the tar. The conditions thereof include preferably a tar concentration in a caustic soda aqueous solution of 1 to 35% by weight and a temperature of 20 to 100° C. When the tar concentration is more than 35% by weight, solid components remain due to incomplete dissolution to cause clogging, and when less than 1% by weight, the amount of the caustic soda aqueous solution increases, leading sometimes to increase in drain treatment cost.

As the caustic soda aqueous solution, caustic soda aqueous solutions turned to unnecessary in the second and third steps can also be re-utilized, and by treating drain together with the caustic soda aqueous solution, the treatment method can realize not only reduction in handling working but also remarkable lowering in cost.

EXAMPLE

Example 1

100 Parts by weight of a 7 wt % caustic soda aqueous solution was charged in a mixing vessel, then 5 parts by weight of tar separated from a liquid containing 1,3-dihydroxybenzene obtained by acidolysis of a liquid containing 1,3-di-(2-hydroxyperoxy-2-propyl) benzene was charged therein. The mixture was stirred at a temperature of about 70° C., and tar was completely dissolved. The 7 wt % caustic soda aqueous solution was used in the second and third steps, and the caustic soda aqueous solution turned to be unnecessary was re-utilized.

Comparative Example 1

Tar separated from a liquid containing 1,3-dihydroxybenzene obtained by acidolysis of a liquid containing 1,3-di-(2-hydroxyperoxy-2-propyl)benzene was charged into a vessel containing water. The charged tar was cooled with water and solidified to remain at the bottom.

As described above, according to the present invention, in a method for treating tar separated from a liquid containing an aromatic hydroxybenzene obtained by acidolysis of a liquid containing an aromatic hydroperoxide, a method in which handling of the tar can be markedly improved by dissolving the above-mentioned tar which is itself solid difficult in handling, with an alkaline aqueous solution to give a liquid, is provided.

Further, a method for treating tar, having an excellent characteristic that there is no problem about working environments and the treatment can be effected at low cost since hands are not required, is provided.

What is claimed is:

1. A method for treating tar, which comprises the following steps of:

(1) oxidizing a liquid containing diisopropylbenzene with air or oxygen in a liquid phase, to convert it into a liquid containing di-(2-hydroperoxy-2-propyl)benzene;

(2) contacting the liquid containing di-(2-hydroperoxy-2-propyl)benzene with an alkaline aqueous solution to obtain an aqueous layer containing di-(2-hydroperoxy-2-propyl)benzene and an oil layer;

(3) contacting the aqueous layer containing a di-(2-hydroperoxy-2-propyl)benzene with an organic solvent as an extracting solvent, to obtain an aqueous layer and an oil layer containing a di-(2-hydroperoxy-2-propyl)benzene extracted from the aqueous layer;

(4) contacting the oil layer thus obtained with an acid to obtain a liquid containing a dihydroxybenzene via acidolysis of the di-(2-hydroperoxy-2-propyl)benzene;

(5) distilling the liquid containing the dihydroxybenzene to separate tar from a low boiling point component containing the organic solvent and the dihydroxybenzene; and (6) mixing the tar with an alkaline aqueous solution to dissolve the tar in the alkaline aqueous solution.

2. The method according to claim 1, wherein the alkaline aqueous solution is a caustic soda aqueous solution.

3. The method according to claim 1, wherein the alkaline aqueous solution has an alkali concentration of 1 to 40% by weight.

4. The method according to claim 1, wherein the diisopropylbennzene, di-(2-hydroperoxy-2-propyl)benzene and dihydroxybenzene are 1,3-diisopropylbenzene, 1,3-di-(2-hydroperoxy-2-propyl)benzene and 1,3-dihydroxybenzene, respectively.

5. The method according to claim 1, wherein the alkaline aqueous solution in the step (6) is a caustic soda aqueous solution.

6. The method according to claim 1, wherein the alkaline aqueous solution containing the tar dissolved therein obtained in the step (6) is subjected to drain treatment.

7. The method according to claim 6, wherein the alkaline aqueous solution containing the tar is a caustic soda aqueous solution containing the same.

8. The method according to claim 7, wherein the concentration of the tar dissolved in the caustic soda aqueous solution is 1 to 35% by weight.

9. The method according to claim 1, wherein the aqueous layer which has been used in the steps of the (2) and (3) is used for dissolving the tar.

* * * * *